United States Patent
Pedersen

(10) Patent No.: US 9,958,404 B2
(45) Date of Patent: May 1, 2018

(54) X-RAY ANALYZING SYSTEM FOR X-RAY SCATTERING ANALYSIS

(71) Applicant: Bruker AXS GmbH, Karlsruhe (DE)

(72) Inventor: Jan Skov Pedersen, Aarhus (DK)

(73) Assignee: Bruker AXS GmbH, Karlsruho (DE)

( * ) Notice: Subject to any disclaimer, the term of this patent is extended or adjusted under 35 U.S.C. 154(b) by 293 days.

(21) Appl. No.: 14/198,611

(22) Filed: Mar. 6, 2014

(65) Prior Publication Data

US 2014/0270079 A1 Sep. 18, 2014

(30) Foreign Application Priority Data

Mar. 15, 2013 (EP) .................................... 13159569

(51) Int. Cl.
*G01N 23/201* (2006.01)
*G21K 1/04* (2006.01)

(52) U.S. Cl.
CPC ............ *G01N 23/201* (2013.01); *G21K 1/04* (2013.01); *G21K 1/046* (2013.01); *G01N 2223/314* (2013.01); *G21K 2201/062* (2013.01)

(58) Field of Classification Search
None
See application file for complete search history.

(56) References Cited

U.S. PATENT DOCUMENTS

| 4,200,799 A * | 4/1980 | Saito ...................... A61B 6/032 378/13 |
| 5,039,867 A * | 8/1991 | Nishihara ............ A61N 5/1042 250/491.1 |
| 2004/0066895 A1 | 4/2004 | Hoshino |
| 2004/0066903 A1* | 4/2004 | Fujinawa ............. G01N 23/201 378/145 |

(Continued)

FOREIGN PATENT DOCUMENTS

| JP | H08145916 | 6/1996 |
| JP | H09119906 | 5/1997 |

OTHER PUBLICATIONS

Jan Skov Pedersen, "A flux- and background-optimized version of the NanoSTAR small-angle X-ray scattering camera for solution scattering", Journal of Applied Crystallography, (2004), 37, 369-380.

(Continued)

*Primary Examiner* — Wyatt Stoffa
*Assistant Examiner* — James Choi
(74) *Attorney, Agent, or Firm* — Paul Vincent

(57) ABSTRACT

An X-ray analyzing system for x-ray scattering analysis having an x-ray source for generating a beam of x-rays propagating along a transmission axis (3), at least one hybrid slit (5b) with an aperture which defines the shape of the cross section of the beam, a sample on which the beam shaped by the hybrid slit (5b) is directed and an X-ray detector for detecting x-rays originating from the sample. The hybrid slit (5b) has at least three hybrid slit elements (7), each hybrid (Continued)

slit element (7) having a single crystal substrate (8) bonded to a base (9) with a taper angle $\alpha \neq 0$. The single crystal substrates (8) of the hybrid slit elements (7) limit the aperture and the hybrid slit elements (7) are staggered with an offset along the transmission axis (3). The X-ray analyzing system has improved resolution and signal to noise ratio.

12 Claims, 4 Drawing Sheets

(56) References Cited

U.S. PATENT DOCUMENTS

| | | | |
|---|---|---|---|
| 2004/0223586 A1* | 11/2004 | He | G01N 23/201 378/86 |
| 2006/0013362 A1* | 1/2006 | Omote | G01B 15/02 378/70 |
| 2006/0126793 A1* | 6/2006 | Li | G21K 1/04 378/152 |
| 2007/0221853 A1* | 9/2007 | Joung | G01T 1/1642 250/363.09 |
| 2008/0118023 A1* | 5/2008 | Besson | A61B 6/06 378/8 |
| 2012/0294426 A1* | 11/2012 | Panine | G01N 23/201 378/84 |
| 2013/0315375 A1* | 11/2013 | Kleine | G01N 23/20008 378/71 |
| 2017/0074809 A1* | 3/2017 | Ito | G01N 23/201 |
| 2017/0315055 A1* | 11/2017 | Tinnemans | G01N 21/47 |

OTHER PUBLICATIONS

Youli Li, et al., "Scatterless hybrid metal-single-crystal slit for small-angle X-ray scattering and high-resolution X-ray diffraction", J. Appl. Cryst. (2008), vol. 41, Pa. 1134-1139.

Y. Li et al., "Scatterless hybrid metal-single-crystal . . .", Journal of Applied Crystallography, (2008), vol. 41, Part 6, pp. 1134-1139.

* cited by examiner

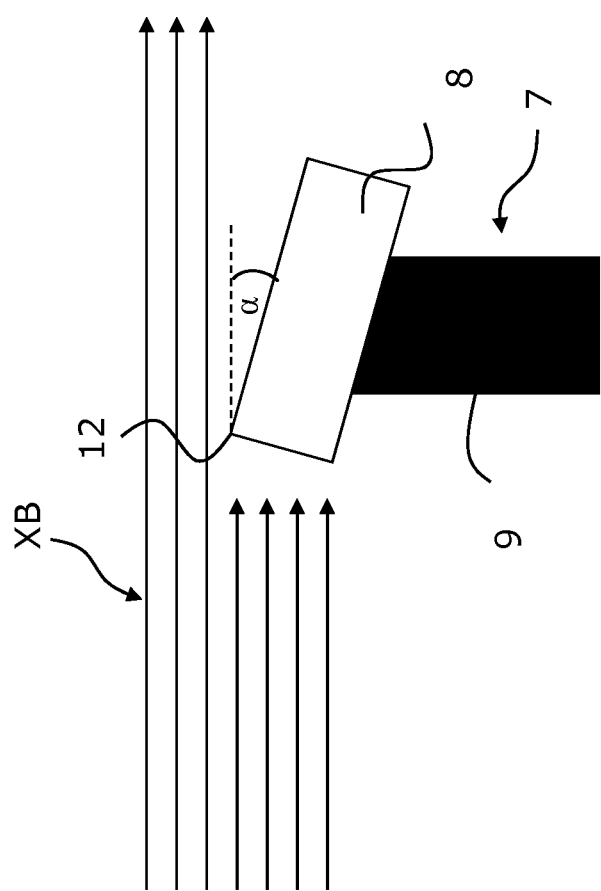

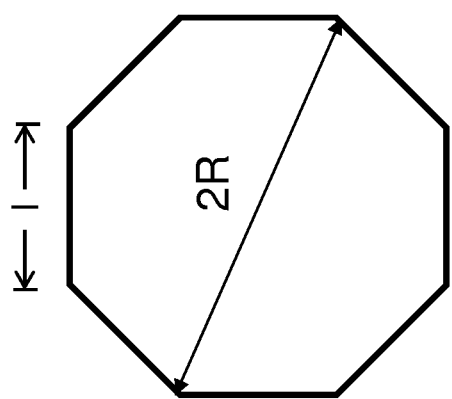

X-RAY ANALYZING SYSTEM FOR X-RAY SCATTERING ANALYSIS

This application claims Paris convention priority from EP 13 159 569.6 filed Mar. 15, 2013, the entire disclosure of which is hereby incorporated by reference.

BACKGROUND OF THE INVENTION

The invention relates to an x-ray analyzing system for x-ray scattering analysis comprising: an x-ray source for generating a beam of x-rays propagating along a transmission axis, at least one hybrid slit with an aperture which defines the shape of the cross-section of the x-ray beam, a sample on which the x-ray beam shaped by the hybrid slit is directed, and an x-ray detector for detecting x-rays originating from the sample, wherein the hybrid slit comprises at least three hybrid slit elements, each hybrid slit element comprising a single crystal substrate bonded to a base with a taper angle $\alpha \neq 0$, the single crystal substrates of the hybrid slit elements limiting the aperture.

Such an x-ray analyzing system is known from WO 2011 086 191 A1.

X-ray measurements, in particular x-ray diffraction (XRD) and small angle x-ray scattering (SAXS) measurements are used for chemical analysis and structural analysis of samples in a variety of applications.

In particular in SAXS measurements using laboratory sources it is important to have a high photon flux and a low background. The photon flux is important to have short data acquisition times and the low background is important since the scattering signal is often very low. The aperture of the slit defines the size and shape of the beam cross-section and the divergence of the beam which are important parameters for the achievable resolution.

By directing x-rays to an aperture of a slit of polycrystalline material parasitic diffraction can happen, which results in a decreased signal to noise ratio. In order to limit the divergence of the x-ray beam it is known to use three aperture slits within the optical path of the x-ray beam. However, this results in a reduction of the photon flux and therefore in an increased measurement time.

Li Youli; Beck Roy; Huang Tuo; et al. (Scatterless hybrid metal-single-crystal slit for small angle x-ray scattering and high resolution x-ray diffraction; JOURNAL OF APPLIED CRYSTALLOGRAPHY Volume: 41 Pages: 1134-1139 (2008)) suggested the use of hybrid slits where the edges are made of single crystals such as Germanium or Silicon. The hybrid slits comprise a metal base on which a rectangular single crystal substrate is mounted, wherein the single crystal substrates of the hybrid slit elements limiting the aperture. Parasitic scattering due to total reflection and scattering at grain boundaries can be avoided. The introduction of hybrid slits has made it possible to use only two slits (square pinholes) and still have a low background.

WO 2011 086 191 A1 discloses an x-ray analyzing system for SAXS measurements using hybrid slits comprising two sets of two hybrid slit elements being arranged opposite with respect to each other to form a rectangular or square aperture. In SAXS measurements the resolution is determined by the smallest achievable scattering angle which in turn depends on the size of the cross-section of the direct beam which is blocked by an appropriate beamstop. Since the minimal beamstop size is determined by the distance from the center to the outermost point of the beam cross-section, the resolution of the x-ray analyzing system known from WO 2011 086 191 A1 is limited by the dimensions of the hybrid slit elements.

It is the object of the invention to suggest an x-ray analyzing system with improved resolution and signal to noise ration.

SUMMARY OF THE INVENTION

In accordance with the invention this object is achieved in that the hybrid slit elements are staggered with an offset along the transmission axis.

The x-ray beam is directed on the sample, whereby the edges of the single crystal substrates of the hybrid slit limits the cross-section of the x-ray beam generated by the x-ray source. Therefore the hybrid slit elements are positioned circumferential around the transmission axis with their basis facing away from the transmission axis and their single crystal substrates facing towards the transmission axis.

Due to the inventive staggered arrangement of the hybrid slit elements the single crystal substrates are positioned at different positions along the transmission axis (offset in z-direction), in which the single crystal substrates may overlap (seen in projection along the transmission axis) without obstructing each other. Thus the size of the aperture of the hybrid slit can be chosen independently of the size of the hybrid slit elements and the shape of the aperture can be chosen independently of the size if the aperture by selecting an appropriate number of hybrid slit elements. Preferably the offset between corresponding parts of the single crystal substrates complies with the dimension of the single crystal substrates in direction of the transmission axis. The offset of the hybrid slit elements then depends on the thickness of the single crystal substrates.

By staggering the hybrid slit elements a polygonal cross-section with a high number of edges can be realized which—in spite of the high number of edges—shows a small size. The bases of the hybrid slit elements are preferably made of high density metal; the single crystal substrates are of high quality in order to ensure a minimum number of material defects (perfect single crystal), preferably the single crystal substrates made of Ge, Si are used.

The hybrid slit, the sample and the detector are preferably positioned along the transmission axis, whereby the sample is positioned between the hybrid slit and the detector. The hybrid slit is positioned within the optical path of the beam between the x-ray source and the sample. It is also possible to displace the detector perpendicular to the optical path in order to measure a wider angular range. In this case the direct beam (beam passing the hybrid slit without being scattered) is directed to the edge of the detector.

In a preferred embodiment the hybrid slit elements are arranged to form a polygon with n edges viewed in projection along the transmission axis, with n>4, in particular n≥8.

Preferably the shape of the cross-section of the beam defined by the aperture is a regular polygon. The higher the number of edges in the polygon, the better it approximates a circle and, thus, the higher the photon flux that will pass it. Due to the increased photon flux the number of slits and thus the size of the analyzing system can be reduced. For a negligible offset of the single crystal substrates the shape of the aperture of the hybrid slit is also a regular polygon and the distances of the single crystal substrates to the transmission axis is the same for all single crystal substrates. With regard of a non-negligible offset the distances d of the single crystal substrates vary in dependence of the position of the single crystal substrates along the transmission axis (Δd=OS tan(2θ) with Δd=difference of distances to transmission axis, 2θ=divergence angle, OS=offset between neighboring single crystal substrates).

In a special embodiment of the inventive x-ray analyzing system the hybrid slit elements are movable perpendicular to the transmission axis, in particular radial. The size and/or shape of the aperture of the hybrid slit can be varied by varying the radial position of the hybrid slit elements.

Since opposing hybrid slit elements do not obstruct each other opposing hybrid slit elements can form a pair and the hybrid slit elements are staggered pairwise. I.e. opposing hybrid slit elements are positioned at the same z-position. Thereby the dimension of the hybrid slit can be reduced.

In a preferred embodiment the x-ray analyzing system is a small angle x-ray diffraction analyzing system comprising a beamstop which is positioned between the hybrid slit and the detector for blocking incident x-rays. For SAXS measurements the detector is positioned close to the transmission axis of the x-ray source in order to detect signals of big nanoparticles. The beamstop is positioned between the sample under investigation and the detector. The beamstop prevents any portion of the direct beam from hitting the detector, which could otherwise saturate the detector and make measurements of the diffracted x-ray energy more difficult. Therefore the beamstop has to be large enough to cover the area that can be hit by the direct beam. On the other hand the scattering angle should be as small as possible and therefore the beamstop is chosen as small as possible.

Preferably the radial positions and the positions along the transmission axis of the hybrid slit elements are chosen to optimize the photon flux of the detected scattered x-rays. Because of the divergence of the x-ray-beam the radial positions of the single hybrid slit elements depend on their respective positions along the transmission axis. In order to optimize the photon flux, the cross-section of the x-ray beam passing the hybrid slit should resemble the shape and size of the beamstop (usually circular).

Most preferably the x-ray source is a laboratory source, e.g. a sealed tube, a rotating anode, a microsource, or a metal-jet source. Laboratory sources show a large divergence which lead to flux losses. In combination with a laboratory source the inventive x-ray analyzing system leads to significant photon flux increase (compared to state of the art x-ray analyzing systems) while the background is still low.

The taper angle is preferably larger than the beam divergence, in particular α>10°. The beam defining single crystal substrate is oriented far from any Bragg peak position with respect to the incident beam in order to inhibit abnormal transmission. In addition the taper angle should be chosen wide enough in order to inhibit surface scattering from the slit.

In a highly preferred embodiment two hybrid slits are provided, wherein the slits are positioned and spaced apart from each other along the transmission axis. Additionally a further slit can be provided, in particular a circular pinhole. The two hybrid slits are preferably separately adjustable in order to adapt the beam cross-section to the requirements of the sample.

The present invention also relates to the use of an inventive apparatus as described above, for optimizing the photon flux in SAXS measurements, in particular using a laboratory source.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

The invention is shown in the drawing.

BRIEF DESCRIPTION OF THE DRAWING

FIG. 2c shows a side view (perpendicular to transmission axis) of a hybrid slit element; and FIG. 3 shows a cross-section of the beam passing an octagonal hybrid slit.

DESCRIPTION OF THE PREFERRED EMBODIMENT

Figure 1:
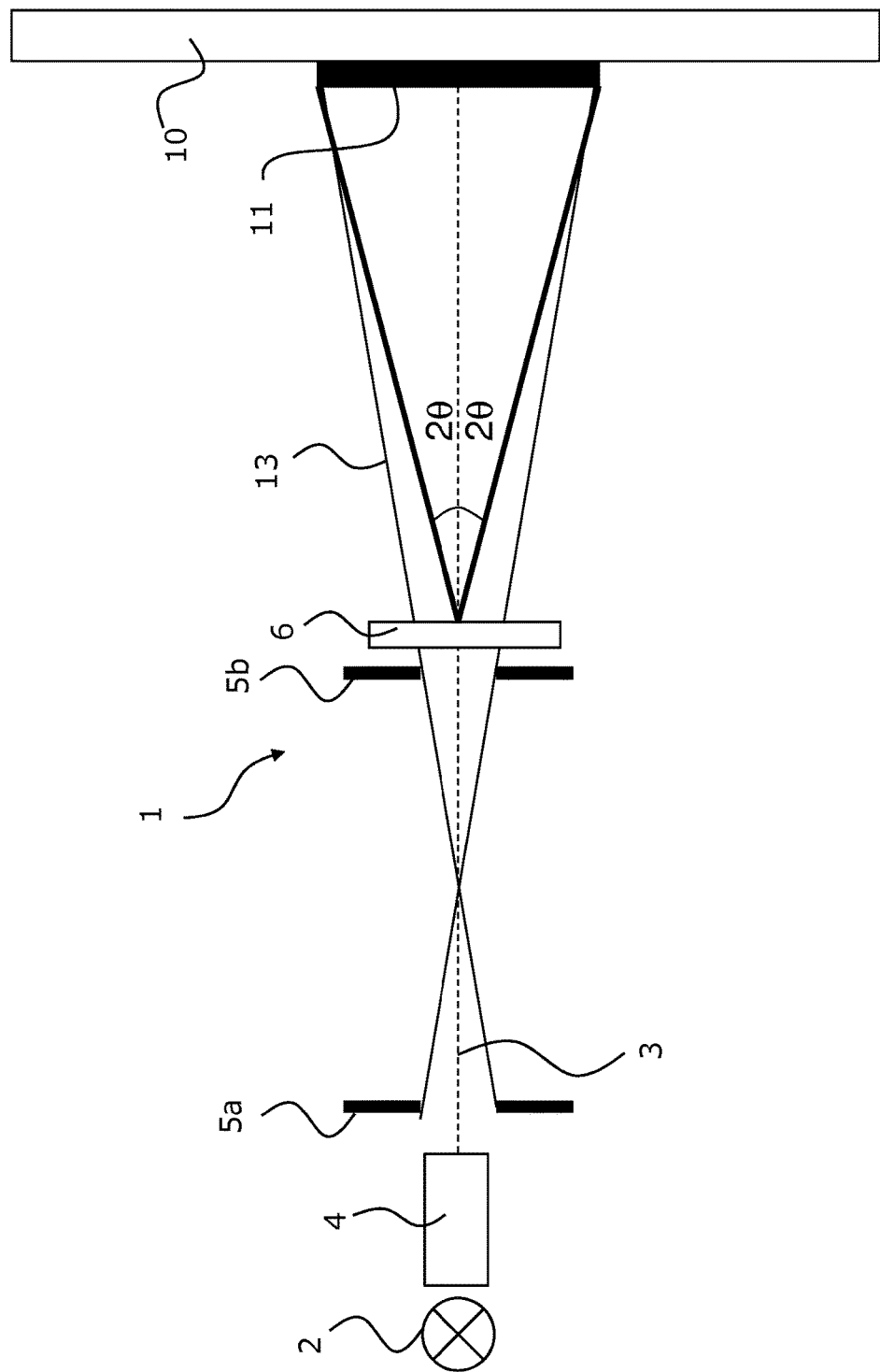
FIG. 1 shows a preferred setup of an inventive x-ray analyzing system.

FIG. 1 shows an embodiment of an inventive x-ray analyzing system 1, e.g. for SAXS measurements. The x-ray analyzing system 1 comprises an x-ray source 2, in particular a laboratory source, emitting an x-ray beam XB along a transmission axis 3. The x-ray beam XB may be prepared by a beam forming element 4 which collects the emitted x-rays, generates a beam of a defined divergence and monochromatism which is then directed to two aperture slits 5a, 5b. The aperture slits 5a, 5b are arranged at a distance along the transmission axis 3 and limit the size of the cross-section of the x-ray beam XB which is directed to a sample 6.

The aperture slit 5b (hybrid slit) which is positioned near the sample 6 comprises several hybrid slit elements 7, which are arranged circumferentially around the transmission axis 3. Each hybrid slit element 7 comprises a single crystal substrate 8 bonded to a base 9 (FIG. 2b). The single crystal substrate 8 is inclined with a taper angle α with respect to the x-ray beam XB (see FIG. 2c). Due to the tilted arrangement of the single crystal substrates 8 the size and shape of the cross-section of the beam XB is defined by sharp edges 12 of the single crystal substrates 8 facing the transmission axis 3. By using hybrid slit elements 7 with single crystal substrates 8 parasitic scattering due to grain boundaries and defects can be avoided. In addition, parasitic scattering due to total reflection can be reduced by choosing the taper angle α of the single crystal substrates 8 wider than the angle of total reflection.

The x-ray beam XB is directed to the sample 6 which is positioned at a distance from the hybrid slit 5b in direction of the transmission axis 3. Scattered x-rays are detected by an x-ray detector 10 (here: position-sensitive area detector) positioned at a distance from the sample 6 in direction of the transmission axis 3. In order to prevent the detector 10 of being saturated, the direct beam XB is blocked by a beamstop 11 positioned between the sample 6 and the detector 10, wherein the transmission axis 3 hits the beamstop 11 at its center.

The size of the polygonal hybrid slit 5b and the size of the beamstop 11 are chosen such, that the most divergent rays 13 (indicated by thin black lines in FIG. 2) of the direct beam XB pass the hybrid slit 5b and the sample 6 is blocked by the beamstop 11. Usually one wants to have the scattering angle 2θ as small as possible and therefore the beamstop 11 should be chosen as small as possible.

Figure 2A:
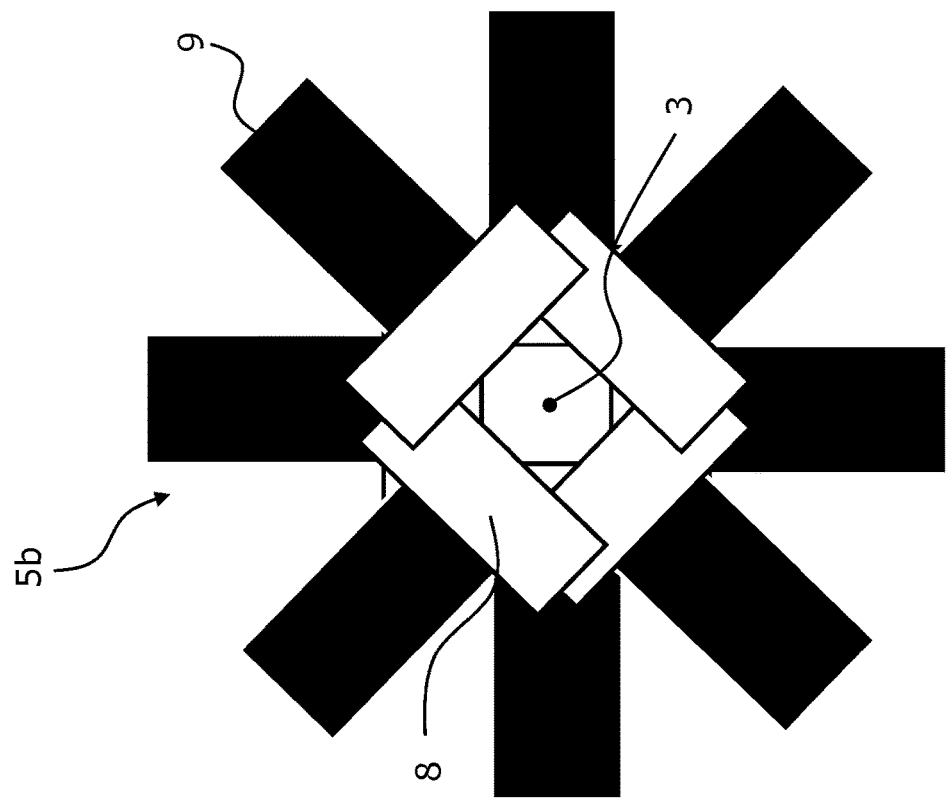
FIG. 2a shows a front view (along transmission axis) of an inventive hybrid slit with an octagonal configuration.
Figure 2B:
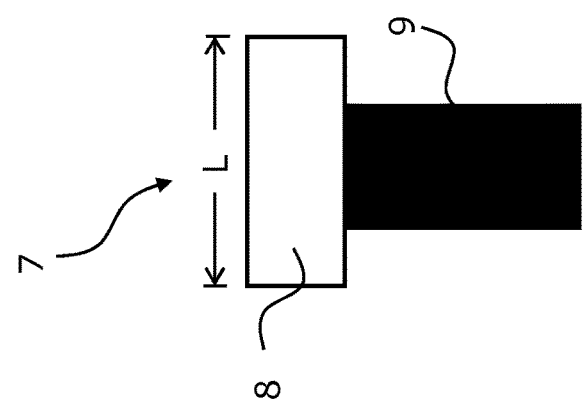
FIG. 2b shows a front view of a single hybrid slit element.

FIG. 2a shows a preferred embodiment of the hybrid slit 5b with eight hybrid slit elements 4. The single crystal substrates 8 of the hybrid slit elements 7 form an octagonal inner contour. Generally for a hybrid slit 5b with a polygonal aperture with n edges at least n hybrid slit elements 7 are required.

According to the invention the hybrid slit elements 7 are staggered with an offset along the transmission axis 3. The staggered arrangement of the hybrid slit elements 7 enables an overlapping arrangement of the hybrid slit elements 7. Thus, small aperture slit sizes can be achieved independently of the size of the single crystal substrates 8 (length l of the aperture edges are not limited to the length L of the single crystal substrates 8—see FIG. 2b, 2c). The offset between two neighboring hybrid slit elements 7 preferably corresponds to the thickness (dimension in direction of the transmission axis 3) of the according single crystal substrate 8 (neighboring single crystal substrates 8 are in contact or nearly in contact with each other). In contrast to the known hybrid slits, an increased number of hybrid slit elements 7 can be provided to form the aperture slit 5b by staggering the hybrid slit elements 7. Thus, the photon flux can be increased by approximating a circular shape, wherein at the same time parasitic scattering can be reduced by using tilted single crystal substrates 8. Yet, the number of hybrid slit elements is limited by the maximal length of the hybrid slit 5b which can be integrated in the x-ray analyzing system.

The aperture slit 5a which is positioned between the source 2 and the hybrid slit 5b can be a circular pinhole, since this increases the total area of the slits and therefore also increases the photon flux. It is almost entirely the hybrid slit 5b that determines the background and therefore only hybrid slit 5b needs to be polygonal, however, both aperture slits 5a, 5b can be polygonal hybrid slits as it will in all cases increase the photon flux, as shown in the following:

For a given size of the beamstop 11 with radius R the maximum diameter of the polygonal hybrid slit 5b is predetermined, since the beamstop 11 has to be able to stop all x-rays that pass the hybrid slit 5b. FIG. 3 shows the cross-section of an x-ray beam that has passed an octagonal hybrid slit configuration 5b. The maximum diameter of the cross-section is 2R.

The higher the number of edges in the polygonal hybrid slit, the better it approximates a circle and, thus, the higher the photon flux that will pass it. The area of a polygon with n sides is:

$$A = \frac{1}{2}nR^2\sin\left(\frac{2\pi}{n}\right)$$

for a square, n=4 the equation gives $A=2R^2$ and for an octagon $A=2.82843 R^2$. For n infinitely large, the polygon approaches a circle for which $A=R^2\pi$. The gain factor in photon flux for using a circular slit for aperture slit 5a and an octagonal hybrid slit for aperture slit 5b is 1.414 and thus 41.4% compared to using a circular slit for aperture slit 5a and a square hybrid slit for aperture slit 5b. The gain factor in photon flux for using a circular slit for aperture slit 5a and an octagonal hybrid slit for aperture slit 5b compared to using two square hybrid slits is 2.221 and thus 122.1%. In experiments gain factors very close to the predicted values have been determined.

The hybrid slit elements 7 can be installed to be movable along the direction of the transmission axis 3 and/or along a radial direction (perpendicular to the transmission axis 3). The latter enables to create different sized and/or shaped hybrid slits 5b in order to adapt the hybrid slit 5b to different applications with different sized beamstops 11. Please note that in order to produce a symmetric cross-section of the x-ray beam different hybrid slit elements 7 have to be arranged at different distances to the transmission axis 3 due to the divergence of the x-ray beam XB and the staggered arrangement of the hybrid slit elements 7. Since the hybrid slit elements 7 are preferable staggered close to each other, the differences of the distances of the hybrid slit elements 7 to the transmission axis 3 are small and not shown in FIG. 2a. Correspondingly, for changing the size but keeping the shape of the aperture of the hybrid slit 5b, the different hybrid slit elements 7 have to be moved by different distances depending on their position along the transmission axis 3, i.e. the further the hybrid slit element 7 are away from the x-ray source 2, the further it has to be moved radially.

The inventive staggered arrangement of hybrid slit elements 7 provides more flexibility concerning size and shape of the aperture of the hybrid slit 5b. A multitude of hybrid slit elements 7 can be used to form a polygonal aperture with a high number of edges, in particular with more than four edges, wherein the length of the edges of the aperture is smaller than the length of the single crystal substrates 8. Thus, the photon flux for a given beamstop size can be increased or the beamstop size can be reduced and the resolution of the x-ray analyzing system 1 can be increased for a given photon flux.

LIST OF REFERENCE NUMBERS 1 x-ray analyzing system
2 x-ray source
3 transmission axis
4 beam forming element
5a aperture slit
5b aperture slit/hybrid slit
6 sample
7 hybrid slit elements
8 single crystal substrate
9 base
10 x-ray detector
11 beamstop
12 sharp edges of the single crystal substrates
13 most divergent x-rays of the x-ray beam
2θ scattering angle
α taper angle
XB x-ray beam

I claim:

1. An SAXS (Small Angle X-ray Scattering) system for x-ray scattering analysis of a sample, the SAXS system comprising:
  an x-ray source for generating a beam of x-rays propagating along a transmission axis in a beam transmission direction;
  a beam forming element disposed downstream of said x-ray source, said beam forming element structured and positioned to collect x-rays emitted from said x-ray source and to generate a beam of defined divergence and monochromatism;
  a first hybrid slit disposed downstream of said beam forming element, said first hybrid slit having a first aperture; and
  a second hybrid slit disposed downstream of and spaced apart from said first hybrid slit, said second hybrid slit having a second aperture, wherein at least one of said first and said second hybrid slits defines a shape of a cross section of said beam incident on the sample by means of at least three hybrid slit elements, each hybrid slit element comprising a single crystal substrate bonded to a base with a taper angle $\alpha \neq 0$, wherein said single crystal substrates of said hybrid slit elements limit said first or second aperture, said hybrid slit elements being staggered with an offset along said transmission axis, wherein each hybrid slit element is adjustable in said beam transmission direction; and an x-ray detector for detecting x-rays originating from the sample, wherein each of said at least three hybrid elements defining the shape of the cross section of said beam incident on the sample is disposed, structured and dimensioned to satisfy the following relationship: $\Delta d = OS \tan(2\theta)$, with $\Delta d$ being a difference between distances to said transmission axis of said beam of neighboring single crystal substrates, $2\theta$ a divergence half-angle of said beam and OS an offset distance between neighboring single crystal substrates in said beam transmission direction, said x-ray source, said beam forming element, said first hybrid slit, said second hybrid slit and said x-ray detector thereby being disposed, structured and dimensioned in order to increase signal to noise ratio in SAXS measurements on the sample.

2. The SAXS system of claim 1, wherein said hybrid slit elements are arranged to form a polygon with n edges viewed in projection along said transmission axis, with n>4.

3. The SAXS system of claim 2, wherein said hybrid slit elements are arranged to form a polygon with n edges viewed in projection along said transmission axis, with n≥8.

4. The SAXS system of claim 2, wherein said shape of said cross section of said beam defined by said first or said second apertures is a regular polygon.

5. The SAXS system of claim 1, wherein said hybrid slit elements are movable perpendicular to said transmission axis.

6. The SAXS system of claim 5, wherein said hybrid slit elements are movable in a radial direction.

7. The SAXS system of claim 1, wherein opposing hybrid slit elements form a pair and said hybrid slit elements are staggered pairwise.

8. The SAXS system of claim 1, further comprising a beamstop which is positioned between said hybrid slit and said detector for blocking incident x-rays.

9. The SAXS system of claim 8, wherein a radial position and a position along said transmission axis of said hybrid slit elements are chosen to optimize a flux of detected, scattered x-rays.

10. The SAXS system of claim 1, wherein said x-ray source is a laboratory source.

11. The SAXS system of claim 1, wherein said taper angle $\alpha$ is larger than a beam divergence $2\theta$.

12. The SAXS system of claim 11, wherein said taper angle $\alpha > 10°$.

* * * * *

UNITED STATES PATENT AND TRADEMARK OFFICE
CERTIFICATE OF CORRECTION

PATENT NO. : 9,958,404 B2
APPLICATION NO. : 14/198611
DATED : May 1, 2018
INVENTOR(S) : Jan Skov Pedersen It is certified that error appears in the above-identified patent and that said Letters Patent is hereby corrected as shown below:

On the Title Page

Item (73), should read:
(73) Assignee: Bruker AXS GmbH, Karlsruhe (DE)

Signed and Sealed this
Thirtieth Day of October, 2018

Andrei Iancu
*Director of the United States Patent and Trademark Office*